United States Patent [19]
Lal et al.

[11] Patent Number: 6,127,146
[45] Date of Patent: Oct. 3, 2000

[54] HUMAN FIBROUS PROTEIN

[75] Inventors: Preeti Lal, Santa Clara; Karl J. Guegler, Menlo Park; Neil C. Corley, Mountain View, all of Calif.

[73] Assignee: Incyte Pharmaceuticals, Inc., Palo Alto, Calif.

[21] Appl. No.: 09/034,177

[22] Filed: Mar. 3, 1998

[51] Int. Cl.[7] .............................. C12P 21/06; C12Q 1/68; C07H 17/00; C07K 14/00
[52] U.S. Cl. .................... 435/69.1; 435/6; 435/252.3; 435/320.1; 435/325; 536/23.1; 530/350
[58] Field of Search .................. 536/23.1; 435/69.1, 435/6, 320.1, 325, 252.3; 530/350

[56] References Cited

PUBLICATIONS

Hillier et al. G I: 884973, May 9, 1995.
Guerette, P.A. et al., "Silk Properties Determined by Gland–Specific Expression of a Spider Fibroin Gene Family" *Science* (1996) 272:112–115.
Hinman, M. et al., "Spider Silk: a Mystery Starting to Unravel" *Results Probl. Cell Differ.* (1992) 19:227–254.
Isselbacher, K.J. et al., *Harrison's Principles of Internal Medicine*, (1994) McGraw–Hill, Inc., New York, NY, pp. 263–264; 2105–2117.
Creighton, T.E., *Proteins, Structures and Molecular Principles* (1984) W.H. Freeman and Company, New York, NY, pp. 191–197.
Lodish, H. et al., *Mol. Cell Biol.* (1995) Scientific American Books, New York, NY, pp. 1106–1116.
Wawersik, M. et al., "A Proline Residue in the α–Helical Rod Domain of Type I Keratin 16 Destabilizes Keratin Heterotetramers" *J. Biol. Chem.* (1997) 272:32557–32565.
Corden, L.D. and McLean, W.H.I., "Human keratin diseases: Hereditary fragility of specific epithelial tissues" *Exp. Dermatol.* (1996) 5:297–307.
Norwood, S.L., "Fibrocystic Breast Disease" *J. Obstet.Gynecol.Neonatal Nurs.* (1990) 19:116–121.
Berkow, R. et al., *The Merck Manual of Medical Information—Home Edition*, (1997) Internet Edition, Section 22, Chapter 234.
Berkow, R. et al., *The Merck Manual of Diagnosis and Therapy*, (1992) Internet Edition, Section 10, Chapter 114; and Section 6, Chapter 68.
Cotran, R.S. et al., *Robbins Pathologic Basis of Disease*, (1994) W.B. Saunders Company, Philadelphia, PA, p. 1243.

*Primary Examiner*—Karen Cochrane Carlson
*Attorney, Agent, or Firm*—Incyte Pharmaceuticals, Inc.

[57] ABSTRACT

The invention provides a human fibrous protein (FIBR) and polynucleotides which identify and encode FIBR. The invention also provides expression vectors, host cells, antibodies, agonists, and antagonists. The invention also provides methods for treating or preventing disorders associated with expression of FIBR.

12 Claims, 10 Drawing Sheets

```
                                    10              19          28          37          46          55
5' G CCG TCA AGC AGG GTA GGA AGA GGA GAG GCC TTG TTT GGA GGA CCT GTT GGG GCC 64          73          82          91          100         109
   AGT GAA CTG GAG CCC TTC AGT CTT TCA TTC CCA GAC CTT ATG GGA GAA CTC
                                                            M   G   E   L 118         127         136         145         154         163
   ATC AGT GAC GAA GCT CCA AGC ATC CCT GCT CCG ACC CCC CAG CTG TCT CCT GCT
   I   S   D   E   A   P   S   I   P   A   P   T   P   Q   L   S   P   A 172         181         190         199         208         217
   CTT AGC ACC ATC ACA GAC TTC TCC CCA GCC GAG TGG TCC TAC CCA GAG GGT GGG GTC
   L   S   T   I   T   D   F   S   P   A   E   W   S   Y   P   E   G   G   V 226         235         244         253         262         271
   AAG GTG CTC ATC ACA GGT CCT TGG ACC GAA GCC GCC GAG CAT TAC TCC TGT GTC
   K   V   L   I   T   G   P   W   T   E   A   A   E   H   Y   S   C   V 280         289         298         307         316         325
   TTT GAT CAC ATC GCA GTG CCA GCC TCA CTT GTC CAG CCT GGT GTC TTA CGC TGC
   F   D   H   I   A   V   P   A   S   L   V   Q   P   G   V   L   R   C 334         343         352         361         370         379
   TAC TGT CCC GCC CAT GAG GTA GGG CTG GTG TCT TTG CAG GTG GCA GGG CGG GAG
   Y   C   P   A   H   E   V   G   L   V   S   L   Q   V   A   G   R   E
```

```
388         397         406         415         424         433
GGG CCC CTT TCT GCT TCT GTG CTC TTT GAG TAT CGA GCC CGC CGA TTC CTG TCT
 G   P   L   S   A   S   V   L   F   E   Y   R   A   R   R   F   L   S 442         451         460         469         478         487
CTG CCT AGT ACT CAA CTT GAC TGG CTG TCA CTG GAC AAC CAG TTC CGG ATG
 L   P   S   T   Q   L   D   W   L   S   L   D   N   Q   F   R   M 496         505         514         523         532         541
TCC ATA CTA GAG CGA CTG GAG CAG ATG GAG AAG ATG GCA GAG ATC GCA GCA
 S   I   L   E   R   L   E   Q   M   E   K   M   A   E   I   A   A 550         559         568         577         586         595
GCT GGG CAG GTG CCT TGC CAG GGT CCT GAT GCT CCT CCA GTT CAG GAT GAA GGC
 A   G   Q   V   P   C   Q   G   P   D   A   P   P   V   Q   D   E   G 604         613         622         631         640         649
CAG GGG CCT GGG TTC GAA GCA CGG CTG GTA GTG GTC TTG GCC CAT GGA AGC ATG ATC CCA
 Q   G   P   G   F   E   A   R   L   V   V   L   A   H   G   S   M   I   P 658         667         676         685         694         703
CGC TCC ACC TGG AAG GGT CCT GAA GCA CGT CTG GCC CAT GGA AGC CCC TTC CGG GGC
 R   S   T   W   K   G   P   E   A   R   L   A   H   G   S   P   F   R   G 712         721         730         739         748         757
ATG AGC CTT CTG CAC CTG GCT GCT GCC CAG GGC TAT GCC CGC CTC ATC GAG ACC
 M   S   L   L   H   L   A   A   A   Q   G   Y   A   R   L   I   E   T
```

```
      766              775         784         793         802              811
CTG AGC CAG TGG CGG AGT GTG GAG ACT GGA AGC TTG GAC TTA GAG CAG GAG GTT
 L   S   Q   W   R   S   V   E   T   G   S   L   D   L   E   Q   E   V 820              829         838         847         856              865
GAC CCG CTC AAC GTG GAT CAT TTC TCT TGC ACC CCT CTG ATG TGG GCT TGT GCC
 D   P   L   N   V   D   H   F   S   C   T   P   L   M   W   A   C   A 874              883         892         901         910              919
CTG GGA CAC CTG GAA GCT GTG CTC TTC TTC CGT TGG AAC CGA CAG GCA CTG
 L   G   H   L   E   A   V   L   F   F   R   W   N   R   Q   A   L 928              937         946         955         964              973
AGC ATT CCC GAC TCT CTG GGC CGT TGC CTG CCA TTG TCT GTG GCT CAT TCC CGG GGT
 S   I   P   D   S   L   G   R   C   L   P   L   S   V   A   H   S   R   G 982              991         1000        1009        1018             1027
CAT GTG CGC CGC CTT GCC TGC CTT GAG GAA CTA CAG AGA CAG GAG CCT TCG GTG
 H   V   R   R   L   A   C   L   E   E   L   Q   R   Q   E   P   S   V 1036             1045        1054        1063        1072             1081
GAG CCC CCA TTT GCC CTA TCG CCA CCC TCC AGC CCA GAC ACT GGT CTG AGC
 E   P   P   F   A   L   S   P   P   S   S   P   D   T   G   L   S 1090             1099        1108        1117        1126             1135
AGC GTC TCC TCG CCC TCG GAG CTG TCG GAT GGC ACC TTT TCC GTC ACG TCA GCC
 S   V   S   S   P   S   E   L   S   D   G   T   F   S   V   T   S   A
```

FIGURE 1C

```
             1144            1153            1162            1171            1180            1189
TAT TCT AGT GCC CCA GAT GGC AGT CCC CCT GCA CCT CTG CCA GCC TCT GAG
 Y   S   S   A   P   D   G   S   P   P   A   P   L   P   A   S   E 1198            1207            1216            1225            1234            1243
ATG ACT ATG GAG GAC ATG GCC ATG GCC CCA GGC CAG CTT TCC TCT GGT GTC CCA GAA GCC
 M   T   M   E   D   M   A   M   A   P   G   Q   L   S   S   G   V   P   E   A 1252            1261            1270            1279            1288            1297
CCC CTA CTC CTC ATG GAC TAT GAG GCT ACC AAC TCC AAG GGG CCC CTC TCC TCC
 P   L   L   L   M   D   Y   E   A   T   N   S   K   G   P   L   S   S 1306            1315            1324            1333            1342            1351
CTT CCT GCC CTC CCA CCA GCT TCA GAT GAT GGG GCT GCT CCG GAG GAC GCT GAC
 L   P   A   L   P   P   A   S   D   D   G   A   A   P   E   D   A   D 1360            1369            1378            1387            1396            1405
AGC CCA CAG GCT GTG GAT GTG ATC CCG GTG GAC ATG ATC TCA CTA GCC AAG CAG
 S   P   Q   A   V   D   V   I   P   V   D   M   I   S   L   A   K   Q 1414            1423            1432            1441            1450            1459
ATC ATC GAA GCC ACA CCG GAG CGG ATT AAA CGA GAG GAC TTC GTG GGG CTG CCC
 I   I   E   A   T   P   E   R   I   K   R   E   D   F   V   G   L   P 1468            1477            1486            1495            1504            1513
GAG GCT GGA GCC TCA ATG CGG GAG CGG ACA GGG GCT GTG GGG CTC AGT GAG ACC
 E   A   G   A   S   M   R   E   R   T   G   A   V   G   L   S   E   T
```

FIGURE 1D

```
      1522            1531            1540            1549            1558            1567
ATG TCC TGG CTG GCC AAC TAC CTG GAG AAT GTG GAC CAT TTC CCC AGC TCA ACC
 M   S   W   L   A   N   Y   L   E   N   V   D   H   F   P   S   S   T 1576            1585            1594            1603            1612            1621
CCT CCC AGC GAA CTG CCC TTT GAG CGA GGT CGC CTG GCT GTC CCT TCA GCA CCC
 P   P   S   E   L   P   F   E   R   G   R   L   A   V   P   S   A   P 1630            1639            1648            1657            1666            1675
TCC TGG GCA GAG TTT CTC TCT GCA TCC ACC AGT GGC AAG ATG GAA AGT GAT TTT
 S   W   A   E   F   L   S   A   S   T   S   G   K   M   E   S   D   F 1684            1693            1702            1711            1720            1729
GCC CTG ACA CTA TCA GAT CAC GAG CAG CGG GAA CTG TAT GAA GGC TGC CCG
 A   L   T   L   S   D   H   E   Q   R   E   L   Y   E   G   C   P 1738            1747            1756            1765            1774            1783
AGT CAT CCA GAC GGC CTT CCG AAA GTA CAA GGG CCG GCG GCT GAA GGA GCA GCA
 S   H   P   D   G   L   P   K   V   Q   G   P   A   A   E   G   A   A 1792            1801            1810            1819            1828            1837
GGT AGC AGC AGC TGT AAT CCA GCG CTG TTA CCG GAA GTA CAA GCA GTT TGC
 G   S   S   S   C   N   P   A   L   L   P   E   V   Q   A   V   C 1846            1855            1864            1873            1882            1891
ACT CTA TAA GAA GAT GAC CCA GGC GGC CAT CCT GAT CCA GAG CAA GTT CCG AAG
 T   L   *
```

FIGURE 1E

```
1900            1909            1918            1927            1936            1945
CTA CTA TGA ACA GAA GCG ATT TCA GCA GAG CCG CCG AGC GGC TGT GCT CAT CCA 1954            1963            1972            1981            1990            1999
GCA GCA CTA CCG CTC CTA CCG CAG GCC CCC TCC CCA CCG GAC TTC GGC 2008            2017            2026            2035            2044            2053
CAC CCT GCC CCG CAA CAA AGG CTC CTT TCT CAC CAA GAA GCA GGA CCA GGC 2062            2071            2080            2089            2098            2107
AGC CCG GAA GAT CAT GAG ATT CCT GCG GCG CTG CCG ACA CAG GAT GAG GGA ACT 2116            2125            2134            2143            2152            2161
GAA GCA GAA CCA GGA AGG GCT GGA AGG GCT TCC CCA GCC GGG ACT GGC CAC ATG ACC 2170            2179            2188            2197            2206            2215
TGG CCA CCG CCT TTC TCA CCA CCC TGG GGG CGC CTC GTG CAG TCT TAA CAG GGA 2224            2233            2242            2251            2260            2269
GAG GGC TTT CTG GGG CAG GGG GAG CCC CAG CTT TCC TGT CGG TCA CCT TTG
```

FIGURE 1F

```
              2278      2287      2296      2305      2314      2323
              TTG GAG CCC TCT GTA GGC CTC CTC CCT CCT CCC CAC GCC TTG CTC CCA CAC CCC 2332      2341      2350      2359      2368      2377
              TCT CCT CGT CCC TCC TGG TCG TGC CCC GTC TCT TTT GGT CCT GGC TCC AGA AAA 2386      2395      2404      2413      2422      2431
              CCC GCG CCC CAC ATA CCT GCA TCT TCC GCT GTG ACC TCC GGA GCC CTG CCT GCC 2440      2449      2458      2467      2476      2485
              CCT GCT CCC CAG CTC CTG CCT GCA CCC GAC TCG GCC CCC TCC TGA CTT GCC 2494      2503      2512      2521      2530      2539
              TTA TTT ATT TGT TCG ACG CGT CTC TGA ATG TAT CCG CCT CGG TTC CCA CCA CTG 2548      2557      2566      2575      2584      2593
              CCT TCG CTG CGC ACG CCC CTC GTG TTT CAG GGC TGA CCG TGT CCC CAC CCG ACT 2602      2611      2620      2629      2638      2647
              CCG CAT GTT TGC GTC TGT TTC CTC CCT CTC TGG CCC TGT CTT ACC CCA TCA CCC
```

FIGURE 1G

```
     2656      2665      2674      2683      2692      2701
GAC TCT GGC CAC TGA CCT CAG GGC CGA AGG GGA GGT GGT GTA CAT AGG AAC GCG 2710      2719      2728      2737      2746      2755
TTG CGG AGT CCG CCC CGT CCC CCG AGG GGA GGG GTC TTG TAC ATA CTG TAA CAT 2764      2773      2782      2791      2800      2809
ACA GAG TAT AGT GAA GAA TCT ATT TAA GGC GCC GCG GGG AGG GCT GCA CGG CCG 2818      2827      2836      2845      2854      2863
GGC TTG TGG TTC TCT AGC GCG GCG GCC TCC TGC CGG CTC CAC GGG CAC TTT 2872      2881      2890      2899      2908
CTA CTT GTG CAT GGG CTT GGT TTA TAC GAA TTG CCA TTA AAC ATC GCT C 3'
```

FIGURE 1H

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 582 amino acids
      (B) TYPE: amino acid
      (C) STRANDEDNESS: single
      (D) TOPOLOGY: linear (vii) IMMEDIATE SOURCE:
      (A) LIBRARY: OVARTUT01
      (B) CLONE: 2257563

(xi) SEQUENCE DESCRIPTION: SEQ ID NO:1:

```
Met Gly Glu Leu Ile Ser Asp Glu Ala Pro Ser Ile Pro Ala Pro Thr
 1               5                  10                  15

Pro Gln Leu Ser Pro Ala Leu Ser Thr Ile Thr Asp Phe Ser Pro Glu
            20                  25                  30

Trp Ser Tyr Pro Glu Gly Gly Val Lys Val Leu Ile Thr Gly Pro Trp
        35                  40                  45

Thr Glu Ala Ala Glu His Tyr Ser Cys Val Phe Asp His Ile Ala Val
    50                  55                  60

Pro Ala Ser Leu Val Gln Pro Gly Val Leu Arg Cys Tyr Cys Pro Ala
65                  70                  75                  80

His Glu Val Gly Leu Val Ser Leu Gln Val Ala Gly Arg Glu Gly Pro
                85                  90                  95

Leu Ser Ala Ser Val Leu Phe Glu Tyr Arg Ala Arg Arg Phe Leu Ser
            100                 105                 110

Leu Pro Ser Thr Gln Leu Asp Trp Leu Ser Leu Asp Asp Asn Gln Phe
        115                 120                 125

Arg Met Ser Ile Leu Glu Arg Leu Glu Gln Met Glu Lys Arg Met Ala
    130                 135                 140

Glu Ile Ala Ala Ala Gly Gln Val Pro Cys Gln Gly Pro Asp Ala Pro
145                 150                 155                 160

Pro Val Gln Asp Glu Gly Gln Gly Pro Gly Phe Glu Ala Arg Val Val
                165                 170                 175

Val Leu Val Glu Ser Met Ile Pro Arg Ser Thr Trp Lys Gly Pro Glu
            180                 185                 190
```

```
Arg Leu Ala His Gly Ser Pro Phe Arg Gly Met Ser Leu Leu His Leu
            195                 200                 205

Ala Ala Ala Gln Gly Tyr Ala Arg Leu Ile Glu Thr Leu Ser Gln Trp
            210                 215                 220

Arg Ser Val Glu Thr Gly Ser Leu Asp Leu Glu Gln Glu Val Asp Pro
225                 230                 235                 240

Leu Asn Val Asp His Phe Ser Cys Thr Pro Leu Met Trp Ala Cys Ala
                245                 250                 255

Leu Gly His Leu Glu Ala Ala Val Leu Leu Phe Arg Trp Asn Arg Gln
            260                 265                 270

Ala Leu Ser Ile Pro Asp Ser Leu Gly Arg Leu Pro Leu Ser Val Ala
            275                 280                 285

His Ser Arg Gly His Val Arg Leu Ala Arg Cys Leu Glu Glu Leu Gln
            290                 295                 300

Arg Gln Glu Pro Ser Val Glu Pro Pro Phe Ala Leu Ser Pro Pro Ser
305                 310                 315                 320

Ser Ser Pro Asp Thr Gly Leu Ser Ser Val Ser Ser Pro Ser Glu Leu
                325                 330                 335

Ser Asp Gly Thr Phe Ser Val Thr Ser Ala Tyr Ser Ser Ala Pro Asp
            340                 345                 350

Gly Ser Pro Pro Pro Ala Pro Leu Pro Ala Ser Glu Met Thr Met Glu
            355                 360                 365

Asp Met Ala Pro Gly Gln Leu Ser Ser Gly Val Pro Glu Ala Pro Leu
            370                 375                 380

Leu Leu Met Asp Tyr Glu Ala Thr Asn Ser Lys Gly Pro Leu Ser Ser
385                 390                 395                 400

Leu Pro Ala Leu Pro Pro Ala Ser Asp Asp Gly Ala Ala Pro Glu Asp
                405                 410                 415

Ala Asp Ser Pro Gln Ala Val Asp Val Ile Pro Val Asp Met Ile Ser
            420                 425                 430

Leu Ala Lys Gln Ile Ile Glu Ala Thr Pro Glu Arg Ile Lys Arg Glu
            435                 440                 445

Asp Phe Val Gly Leu Pro Glu Ala Gly Ala Ser Met Arg Glu Arg Thr
            450                 455                 460

Gly Ala Val Gly Leu Ser Glu Thr Met Ser Trp Leu Ala Asn Tyr Leu
465                 470                 475                 480

Glu Asn Val Asp His Phe Pro Ser Ser Thr Pro Ser Glu Leu Pro
                485                 490                 495

Phe Glu Arg Gly Arg Leu Ala Val Pro Ser Ala Pro Ser Trp Ala Glu
            500                 505                 510

Phe Leu Ser Ala Ser Thr Ser Gly Lys Met Glu Ser Asp Phe Ala Leu
            515                 520                 525

Leu Thr Leu Ser Asp His Glu Gln Arg Glu Leu Tyr Glu Gly Cys Pro
            530                 535                 540

Ser His Pro Asp Gly Leu Pro Lys Val Gln Gly Pro Ala Ala Glu Gly
545                 550                 555                 560

Ala Ala Gly Gly Ser Ser Ser Cys Asn Pro Ala Leu Leu Pro Glu Val
                565                 570                 575

Gln Ala Val Cys Thr Leu
            580
```

(2) INFORMATION FOR SEQ ID NO:2:

(i) SEQUENCE CHARACTERISTICS:
        (A) LENGTH: 2912 base pairs
        (B) TYPE: nucleic acid
        (C) STRANDEDNESS: single
        (D) TOPOLOGY: linear (vii) IMMEDIATE SOURCE:
        (A) LIBRARY: OVARTUT01
        (B) CLONE: 2257563

(xi) SEQUENCE DESCRIPTION: SEQ ID NO:2:

```
GCCGTCAAGC AGGGTAGGAA GAGGAGAGGC CTTGTTTGGA GGACCTGTTG GGGCCAGTGA          60

ACTGGAGCCC TTCAGTCTTT CATCATTCCC AGACCTTATG GGAGAACTCA TCAGTGACGA         120

AGCTCCAAGC ATCCCTGCTC CGACCCCCCA GCTGTCTCCT GCTCTTAGCA CCATCACAGA         180

CTTCTCCCCA GAGTGGTCCT ACCCAGAGGG TGGGGTCAAG GTGCTCATCA CAGGTCCTTG         240

GACCGAAGCC GCCGAGCATT ACTCCTGTGT CTTTGATCAC ATCGCAGTGC CAGCCTCACT         300

TGTCCAGCCT GGTGTCTTAC GCTGCTACTG TCCCGCCCAT GAGGTAGGGC TGGTGTCTTT         360

GCAGGTGGCA GGGCGGGAGG GGCCCCTTTC TGCTTCTGTG CTCTTTGAGT ATCGAGCCCG         420

CCGATTCCTG TCTCTGCCTA GTACTCAACT TGACTGGCTG TCACTGGACG ACAACCAGTT         480

CCGGATGTCC ATACTAGAGC GACTGGAGCA GATGGAGAAG CGGATGGCAG AGATCGCAGC         540

AGCTGGGCAG GTGCCTTGCC AGGGTCCTGA TGCTCCTCCA GTTCAGGATG AAGGCCAGGG         600

GCCTGGGTTC GAAGCACGGG TAGTGGTCTT GGTAGAAAGC ATGATCCCAC GCTCCACCTG         660

GAAGGGTCCT GAACGTCTGG CCCATGGAAG CCCCTTCCGG GGCATGAGCC TTCTGCACCT         720

GGCTGCTGCC CAGGGCTATG CCCGCCTCAT CGAGACCCTG AGCCAGTGGC GGAGTGTGGA         780

GACTGGAAGC TTGGACTTAG AGCAGGAGGT TGACCCGCTC AACGTGGATC ATTTCTCTTG         840

CACCCCTCTG ATGTGGGCTT GTGCCCTGGG ACACCTGGAA GCTGCTGTGC TCCTTTTCCG         900

TTGGAACCGA CAGGCACTGA GCATTCCCGA CTCTCTGGGC CGTCTGCCAT TGTCTGTGGC         960

TCATTCCCGG GGTCATGTGC GCCTTGCCCG CTGCCTTGAG GAACTACAGA GACAGGAGCC        1020

TTCGGTGGAG CCCCCATTTG CCCTATCGCC ACCCTCCTCC AGCCCAGACA CTGGTCTGAG        1080

CAGCGTCTCC TCGCCCTCGG AGCTGTCGGA TGGCACCTTT TCCGTCACGT CAGCCTATTC        1140

TAGTGCCCCA GATGGCAGTC CCCCCCCTGC ACCTCTGCCA GCCTCTGAGA TGACTATGGA        1200

GGACATGGCC CCAGGCCAGC TTTCCTCTGG TGTCCCAGAA GCCCCCCTAC TCCTCATGGA        1260

CTATGAGGCT ACCAACTCCA AGGGGCCCCT CTCCTCCCTT CCTGCCCTCC CACCAGCTTC        1320

AGATGATGGG GCTGCTCCGG AGGACGCTGA CAGCCCACAG GCTGTGGATG TGATCCCGGT        1380

GGACATGATC TCACTAGCCA AGCAGATCAT CGAAGCCACA CCGGAGCGGA TTAAACGAGA        1440

GGACTTCGTG GGGCTGCCCG AGGCTGGAGC CTCAATGCGG GAGCGGACAG GGGCTGTGGG        1500

GCTCAGTGAG ACCATGTCCT GGCTGGCCAA CTACCTGGAG AATGTGGACC ATTTCCCCAG        1560

CTCAACCCCT CCCAGCGAAC TGCCCTTTGA GCGAGGTCGC CTGGCTGTCC CTTCAGCACC        1620

CTCCTGGGCA GAGTTTCTCT CTGCATCCAC CAGTGGCAAG ATGGAAAGTG ATTTTGCCCT        1680

GCTGACACTA TCAGATCACG AGCAGCGGGA ACTGTATGAA GGCTGCCCGA GTCATCCAGA        1740

CGGCCTTCCG AAAGTACAAG GGCCGGCGGC TGAAGGAGCA GCAGGAGGTA GCAGCAGCTG        1800

TAATCCAGCG CTGTTACCGG AAGTACAAGC AGTTTGCACT CTATAAGAAG ATGACCCAGG        1860

CGGCCATCCT GATCCAGAGC AAGTTCCGAA GCTACTATGA ACAGAAGCGA TTTCAGCAGA        1920

GCCGCCGAGC GGCTGTGCTC ATCCAGCAGC ACTACCGCTC CTACCGCCGC AGGCCCGGCC        1980

CTCCCCACCG GACTTCGGCC ACCCTGCCTG CCCGCAACAA AGGCTCCTTT CTCACCAAGA        2040
```

-continued

```
AGCAGGACCA GGCAGCCCGG AAGATCATGA GATTCCTGCG GCGCTGCCGA CACAGGATGA      2100

GGGAACTGAA GCAGAACCAG GAGCTGGAAG GGCTTCCCCA GCCGGGACTG GCCCACATGAC     2160

CTGGCCACCG CCTTTCTCAC CACCCTGGGG GCGCCTCGTG CAGTCTTAAC AGGGAGAGGG      2220

CTTTCTGGGG CAGGGGGAGC CCTGTCGGCA GCTTTCCTGT TCACCTTTGT TGGAGCCCTC      2280

TGTAGGCCTC CTCCCTCCTC CCCACGCCTT GCTCCCACAC CCCTCTCCTC GTCCCTCCTG      2340

GTCGTGCCCC GTCTCTTTTG GTCCTGGCTC CAGAAAACCC GCGCCCCACA TACCTGCATC      2400

TTCCGCTGTG ACCTCCGGAG CCCTGCCTGC CCCTGCTCCC CAGCTCCTCC TGCCTGCACC      2460

CGACTCGGCC CCCTCCTGAC TTGCCTTATT TATTTGTTCG ACGCGTCTCT GAATGTATCC      2520

GCCTCGGTTC CCACCACTGC CTTCGCTGCG CACGCCCCTC GTGTTTCAGG GCTGACCGTG      2580

TCCCCACCCG ACTCCGCATG TTTGCGTCTG TTTCCTCCCT CTCTGGCCCT GTCTTACCCC      2640

ATCACCCGAC TCTGGCCACT GACCTCAGGG CCGAAGGGGA GGTGGTGTAC ATAGGAACGC      2700

GTTGCGGAGT CCGCCCCGTC CCCCGAGGGG AGGGGTCTTG TACATACTGT AACATACAGA      2760

GTATAGTGAA GAATCTATTT AAGGCGCCGC GGGGAGGGCT GCACGGCCGG GCTTGTGGTT      2820

CTCTAGCGCG GCGGGGGCCT CCTGCCGGCT CCACGGGCAC TTTCTACTTG TGCATGGGCT      2880

TGGTTTATAC GAATTGCCAT TAAACATCGC TC                                   2912
```

(2) INFORMATION FOR SEQ ID NO:3:

(i) SEQUENCE CHARACTERISTICS:
        (A) LENGTH: 747 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI 1174414

(xi) SEQUENCE DESCRIPTION: SEQ ID NO:3:

```
Gln Gly Ala Gly Ala Ala Ala Ala Ala Gly Gly Ala Gly Gln Gly
 1               5                  10                  15

Gly Tyr Gly Gly Leu Gly Gly Gln Gly Ala Gln Gly Gly Tyr Gly
                20                  25                  30

Gly Leu Gly Gly Gln Gly Ala Gly Gln Gly Ala Gly Ala Ala Ala
        35                  40                  45

Ala Ala Ala Gly Gly Ala Gly Gln Gly Gly Tyr Gly Gly Leu Gly Ser
 50                  55                  60

Gln Gly Ala Gly Arg Gly Gly Gln Gly Ala Gly Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
            100                 105                 110

Ala Ala Ala Gly Gly Ala Gly Gln Gly Gly Tyr Gly Gly Leu Gly Asn
            115                 120                 125

Gln Gly Ala Gly Arg Gly Gly Gln Gly Ala Ala Ala Ala Ala Gly
            130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala
                165                 170                 175
```

-continued

```
Gly Gly Ala Gly Gln Gly Gly Tyr Gly Gly Leu Gly Gly Gln Gly Ala
            180                 185                 190
Gly Gln Gly Gly Tyr Gly Gly Leu Gly Ser Gln Gly Ala Gly Arg Gly
            195                 200                 205
Gly Leu Gly Gly Gln Gly Ala Gly Ala Ala Ala Ala Ala Ala Ala Gly
            210                 215                 220
Gly Ala Gly Gln Gly Gly Leu Gly Gly Gln Gly Ala Gly Gln Gly Ala
225                 230                 235                 240
Gly Ala Ser Ala Ala Ala Gly Gly Ala Gln Gly Gly Tyr Gly
            245                 250                 255
Gly Leu Gly Ser Gln Gly Ala Gly Arg Gly Gly Glu Gly Ala Gly Ala
            260                 265                 270
Ala Ala Ala Ala Gly Gly Ala Gly Gln Gly Gly Tyr Gly Gly Leu
        275                 280                 285
Gly Gly Gln Gly Ala Gly Gln Gly Gly Tyr Gly Gly Leu Gly Ser Gln
            290                 295                 300
Gly Ala Gly Arg Gly Gly Leu Gly Gly Gln Gly Ala Gly Ala Ala Ala
305                 310                 315                 320
Ala Gly Gly Ala Gly Gln Gly Gly Leu Gly Gly Gln Gly Ala Gly Gln
                325                 330                 335
Gly Ala Gly Ala Ala Ala Ala Ala Ala Gly Gly Ala Gly Gln Gly Gly
            340                 345                 350
Tyr Gly Gly Leu Gly Ser Gln Gly Ala Gly Arg Gly Gly Leu Gly Gly
            355                 360                 365
Gln Gly Ala Gly Ala Val Ala Ala Ala Ala Gly Gly Ala Gly Gln
        370                 375                 380
Gly Gly Tyr Gly Gly Leu Gly Ser Gln Gly Ala Gly Arg Gly Gly Gln
385                 390                 395                 400
Gly Ala Gly Ala Ala Ala Ala Ala Gly Gly Ala Gly Gln Arg Gly
                405                 410                 415
Tyr Gly Gly Leu Gly Asn Gln Gly Ala Gly Arg Gly Gly Leu Gly Gly
            420                 425                 430
Gln Gly Ala Gly Ala Ala Ala Ala Ala Ala Gly Gly Ala Gly Gln
        435                 440                 445
Gly Gly Tyr Gly Gly Leu Gly Asn Gln Gly Ala Gly Arg Gly Gly Gln
        450                 455                 460
Gly Ala Ala Ala Ala Ala Gly Gly Ala Gly Gln Gly Gly Tyr Gly Gly
465                 470                 475                 480
Leu Gly Ser Gln Gly Ala Gly Arg Gly Gly Gln Gly Ala Gly Ala Ala
                485                 490                 495
Ala Ala Ala Ala Val Gly Ala Gly Gln Glu Gly Ile Arg Gly Gln Gly
                500                 505                 510
Ala Gly Gln Gly Gly Tyr Gly Gly Leu Gly Ser Gln Gly Ser Gly Arg
            515                 520                 525
Gly Gly Leu Gly Gly Gln Gly Ala Gly Ala Ala Ala Ala Ala Gly
            530                 535                 540
Gly Ala Gly Gln Gly Gly Leu Gly Gly Gln Gly Ala Gly Gln Gly Ala
545                 550                 555                 560
Gly Ala Ala Ala Ala Ala Gly Gly Val Arg Gln Gly Gly Tyr Gly
                565                 570                 575
Gly Leu Gly Ser Gln Gly Ala Gly Arg Gly Gly Gln Gly Ala Gly Ala
            580                 585                 590
Ala Ala Ala Ala Ala Gly Gly Ala Gly Gln Gly Gly Tyr Gly Gly Leu
```

-continued

```
                       595                      600                      605
Gly Gly Gln Gly Val Gly Arg Gly Gly Leu Gly Gly Gln Gly Ala Gly
            610                     615                 620

Ala Ala Ala Ala Gly Gly Ala Gly Gln Gly Gly Tyr Gly Gly Val Gly
625                     630                     635                     640

Ser Gly Ala Ser Ala Ala Ser Ala Ala Ala Ser Arg Leu Ser Ser Pro
                645                     650                     655

Gln Ala Ser Ser Arg Val Ser Ser Ala Val Ser Asn Leu Val Ala Ser
            660                     665                 670

Gly Pro Thr Asn Ser Ala Ala Leu Ser Ser Thr Ile Ser Asn Val Val
            675                     680                 685

Ser Gln Ile Gly Ala Ser Asn Pro Gly Leu Ser Gly Cys Asp Val Leu
            690                     695                 700

Ile Gln Ala Leu Leu Glu Val Val Ser Ala Leu Ile Gln Ile Leu Gly
705                     710                     715                     720

Ser Ser Ser Ile Gly Gln Val Asn Tyr Gly Ser Ala Gly Gln Ala Thr
                725                     730                     735

Gln Ile Val Gly Gln Ser Val Tyr Gln Ala Leu
            740                     745
```

HUMAN FIBROUS PROTEIN

FIELD OF THE INVENTION

This invention relates to nucleic acid and amino acid sequences of a human fibrous protein and to the use of these sequences in the diagnosis, treatment, and prevention of connective tissue disorders, reproductive disorders, cancer, and autoimmune/inflammatory disorders.

BACKGROUND OF THE INVENTION

Fibrous proteins, which serve a structural role in organisms, have a rodlike conformation composed of regular α-helical, triple helical, or β-sheet/β-turn secondary structure. The primary structure contains repeated sequences of amino acids. Fibrous proteins include fibroin, collagen, keratin, myosin, tropomyosin and fibrinogen.

Specialized fibrous proteins in insects constitute cocoon, web, and dragline silk. Silks are composed of cross-linked fibroin proteins whose structure is largely β-sheet and β-turn. Seven similar fibroin genes from spiders have been identified. By varying the pattern of expression of these different fibroins, spiders can produce silks of varying mechanical properties. The fibroin proteins have a pattern of alternating polyalanine or poly(glycinealanine) blocks and glycine-rich blocks. Hydrophobicity analysis shows a characteristic pattern of alternating hydrophobic and hydrophilic regions. (Guerette, P. A. et al. (1996) Science 272:112–115; and Hinman, M. et al. (1992) Results Probl. Cell Differ. 19:227–254.)

Collagen provides structure to bone, teeth, skin, ligaments, tendons, cartilage, blood vessels, and basement membranes. Multiple collagen proteins have been identified. Three collagen molecules fold together in a triple helix stabilized by interchain disulfide bonds. Bundles of these triple helices then associate to form fibrils. Collagen primary structure consists of hundreds of (Gly-X-Y) repeats where about a third (f the X and Y residues are Pro. Glycines are crucial to helix formation as the bulkier amino acid sidechains cannot fold into the triple helical conformation. Because of these strict sequence requirements, mutations in collagen genes have severe consequences. Osteogenesis imperfecta patients have brittle bones that fracture easily; in severe cases patients die in utero or at birth. Ehlers-Danlos syndrome patients have hyperelastic skin, hypermobile joints, and susceptibility to aortic and intestinal rupture. Chondrodysplasia patients have short stature and ocular disorders. Alport syndrome patients have hematuria, sensorineural deafness, and eye lens deformation. (Isselbacher, K. J. et al. (1994) *Harrison's Principles of Internal Medicine*, McGraw-Hill, Inc., New York, N.Y., pp. 2105–2117; and Creighton, T. E. (1984) *Proteins, Structures and Molecular Principles*, W.H. Freeman and Company, New York, N.Y., pp. 191–197.)

Keratin filaments, produced by epithelial cells, form the structural core of the outer layer of skin. This layer protects the dermis from desiccation and abrasion. Two keratin monomers dimerize to form an α-helical coiled coil. These coiled coil dimers associate in a series of steps to form filaments. The keratin primary structure shows a characteristic seven residue (heptad) repeat with hydrophobic residues predominating at positions 1 and 4. Mutations in keratin genes lead to epithelial diseases including epidermolysis bullosa simplex, bullous congenital ichthyosiform erythroderma (epidermolytic hyperkeratosis), non-epidermolytic and epidermolytic palmoplantar keratoderma, ichthyosis bullosa of Siemens, pachyonychia congenita, and white sponge nevus. Some of these diseases result in severe skin blistering. (Lodish, H. et al. (1995) *Molecular Cell Biology*, Scientific American Books, New York, N.Y., pp. 1106–1116; Wawersik, M. et al. (1997) J. Biol. Chem. 272:32557–32565; and Corden L. D. and McLean, W. H. (1996) Exp. Dermatol. 5:297–307.)

In other disorders the pathology is derived from inappropriate deposition of fibrous proteins. Fibrocystic breast disease, whose cause is unknown. is characterized by breast pain, lumpiness, and cysts and may predispose women toward breast cancer. (Norwood, S. L. (1990) J. Obstet. Gynecol. Neonatal Nurs. 19:116–121.) Uterne fibroids, non-cancerous growths of muscle and fibrous tissue in the wall of the uterus, occur in at least 20 percent of all women over age 35. Their cause is unknown, but estrogen levels appear to affect fibroid size. Fibroids may cause heavy or prolonged menstrual bleeding, anemia, infertility, miscarriage, early labor, and postpartum hemorrhage. (Berkow, R. et al. (1997) *The Merck Manual of Medical Information Home Edition*, Internet Edition, Section 22, Chapter 234.) Fibrosis of the penile corpora cavernosa in Peyronie's disease can cause impotence. (Isselbacher, supra, pp. 263–264.) Fibrosis in the palmar fascia (of the hand) in Dupuyten's contracture can cause loss of finger function. (Berkow, R. et al. (1992) *The Merck Manual of Diagnosis and Therapy*, Internet Edition, Section 10, Chapter 114, Tendinitis and Tenosynovitis, Dupuytren's Contracture.) Systemic sclerosis is characterized by fibrosis of the skin, blood vessels, gastrointestinal tract, lungs, heart, and kidneys. Patients suffer from skin thickening, pain, swelling, and stiffness of the fingers and knees, esophageal dysfunction, pulmonary hypertension, and renal failure, and there is no known cure. The cause is unknown but overproduction and accumulation of collagen and other extracellular matrix proteins are observed. (Isselbacher, supra, pp. 1655–1661.) Hepatic fibrosis occurs as a response to hepatocellular necrosis or injury; collagen accumulation leads to hepatic cell atrophy and disruption of hepatic blood flow. (Berkow, R. et al. (1992) *The Merck Manual of Diagnosis and Therapy*, Internet Edition, Section 6, Chapter 68, Fibrosis, Etiology, Pathogenesis.) Collagen is produced in two bone cancers, fibrosarcoma and malignant fibrous histiocytoma. (Cotran, R. S. et al. (1994) *Robbins Pathologic Basis of Disease*, W.B. Saunders Company, Philadelphia, Pa., p. 1243.)

The discovery of a new human fibrous protein and the polynucleotides encoding it satisfies a need in the art by providing new compositions which are useful in the diagnosis, treatment, and prevention of connective tissue disorders, reproductive disorders, cancer, and autoimmune/inflammatory disorders.

SUMMARY OF THE INVENTION

The invention is based on the discovery of a new human fibrous protein (FIBR), the polynucleotides encoding FIBR, and the use of these compositions for the diagnosis, treatment, or prevention of connective tissue disorders, reproductive disorders, cancer, and autoimmune/inflammatory disorders.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide sequence identity to the polynucleotide encoding the polypeptide comprising the amino acid sequence of SEQ ID NO:1 or a fragment of SEQ ID NO:1.

Additionally, the invention provides a composition comprising a polynucleotide encoding the polypeptide comprising the amino acid sequence of SEQ ID NO:1 or a fragment of SEQ ID NO:1. The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 90% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing ar expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a connective tissue disorder associated with the decreased expression or activity of a human fibrous protein (FIBR), the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a connective tissue disorder associated with the increased expression or activity of FIBR, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing a reproductive disorder, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing a cancer, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing an autoimmune/inflammatory disorder, the method comprising administering to a subject in need of such treatment an effective amount of an antagonist of the polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, the nucleic acids of the biological sample are amplified by the polymerase chain reaction prior to the hybridizing step.

BRIEF DESCRIPTION OF THE FIGURES

FIGS. 1A–1H shows the amino acid sequence (SEQ ID NO:1) and nucleic acid sequence (SEQ ID NO:2) of FIBR. The alignment was produced using MacDNASIS PRO™ software (Hitachi Software Engineering Co. Ltd., San Bruno, Calif.).

DESCRIPTION OF THE INVENTION

Figure 2A:
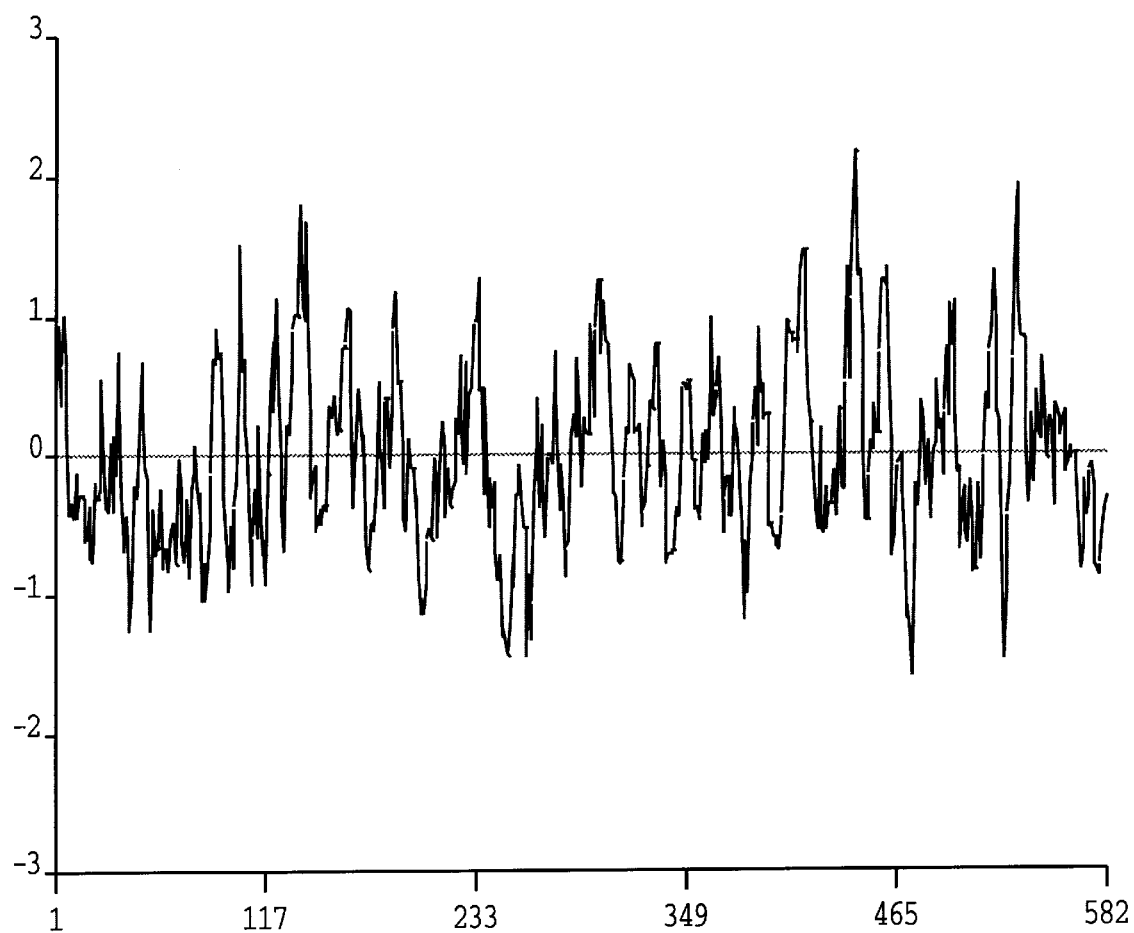
FIGS. 2A and 2B show the hydrophobicity plots of FIBR (2257563; SEQ ID NO:1) and *Nephila clavipes* dragline silk fibroin 1 (GI 1174414; SEQ ID NO:3) respectively, produced using MacDNASIS PRO™ software. The X axis reflects amino acid position, and the Y axis, hydrophobicity, where hydrophobic residues have negative values and hydrophilic residues have positive values.

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"FIBR," as used herein, refers to the amino acid sequences of substantially purified FIBR obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to FIBR, increases or prolongs the duration of the effect of FIBR. Agonists may include proteins, nucleic acids, carbohydrates, or any other molecules which bind to and modulate the effect of FIBR.

An "allele" or an "allelic sequence," as these terms are used herein, is an alternative form of the gene encoding FIBR. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding FIBR, as described herein, include those sequences with deletions, insertions, or substitutions of different nucleotides, resulting in a polynucleotide the same FIBR or a polypeptide with at least one functional characteristic of FIBR. Included within this definition are polymorphisms which may or may not be readily detectable using a particular oligonucleotide probe of the polynucleotide encoding FIBR, and improper or unexpected hybridization to alleles, with a locus other than the normal chromosomal locus for the polynucleotide sequence encoding FIBR. The encoded protein may also be "altered," and may contain deletions, insertions, or substitutions of amino acid residues which produce a silent change and result in a functionally equivalent FIBR. Deliberate amino acid substitutions may be made on the basis of similarity in polarity, charge, solubility, hydrophobicity, hydrophilicity, and/or the amphipathic nature of the residues, as long as the biological or immunological activity of FIBR is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of FIBR which are preferably about 5 to about 15 amino acids in length and which retain some biological activity or immunological activity of FIBR. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.)

The term "antagonist," as it is used herein, refers to a molecule which, when bound to FIBR, decreases the amount or the duration of the effect of the biological or immunological activity of FIBR. Antagonists may include proteins, nucleic acids, carbohydrates, antibodies, or any other molecules which decrease the effect of FIBR.

As used herein, the term "antibody" refers to intact molecules as well as to fragments thereof, such as Fa, F(ab')$_2$, and Fv fragments, which are capable of binding the epitopic determinant. Antibodies that bind FIBR polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by an) method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic FIBR, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding FIBR or fragments of FIBR may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding FIBR, by northern analysis is indicative of the presence of nucleic acids encoding FIBR in a sample, and thereby correlates with expression of the transcript from the polynucleotide encoding FIBR.

A "deletion," as the term is used herein, refers to a change in the amino acid or nucleotide sequence that results in the absence of one or more amino acid residues or nucleotides.

The term "derivative," as used herein, refers to the chemical modification of FIBR, of polynucleotide sequence encoding FIBR, or of a polynucleotide sequence complementary to polynucleotide sequence encoding FIBR. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of nonspecific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign program (DNASTAR, Inc., Madison Wis.). The MegAlign program can create alignments between two or more sequences according to different methods, e.g., the Clustal method. (See, e.g., Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g. the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex", refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element", as used herein in a microarray context, refer to hybridizable polynucleotides arranged on the surface of a substrate.

The term "modulate," as it appears herein, refers to a change in the activity of FIBR. For example, modulation may cause an increase or a decrease in protein activity, binding characteristics, or any other biological, functional, or immunological properties of FIBR.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding FIBR, or fragments thereof, or FIBR itself, may comprise a bodily fluid; an extract from a cell; chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of FIBR, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human fibrous protein (FIBR), the polynucleotides encoding FIBR, and the use of these compositions for the diagnosis, treatment, or prevention of connective tissue disorders, reproductive disorders, cancer, and autoimmune/inflammatory disorders.

Nucleic acids encoding the FIBR of the present invention were first identified in Incyte Clone 2257563 from the ovarian tumor tissue cDNA library (OVARTUT01) using a computer search for amino acid sequence alignments. A consensus sequence, SEQ ID NO:2, was derived from the following overlapping and/or extended nucleic acid sequences: Incyte Clones 1382532 (BRAITUT08), 1509164 (LUNGNOT14), 1903874 (OVARNOT07), 1967003 (BRSTNOT04), 2081292 (UTRSNOT08), and 2257563 (OVARTUT01).

Figure 2B:
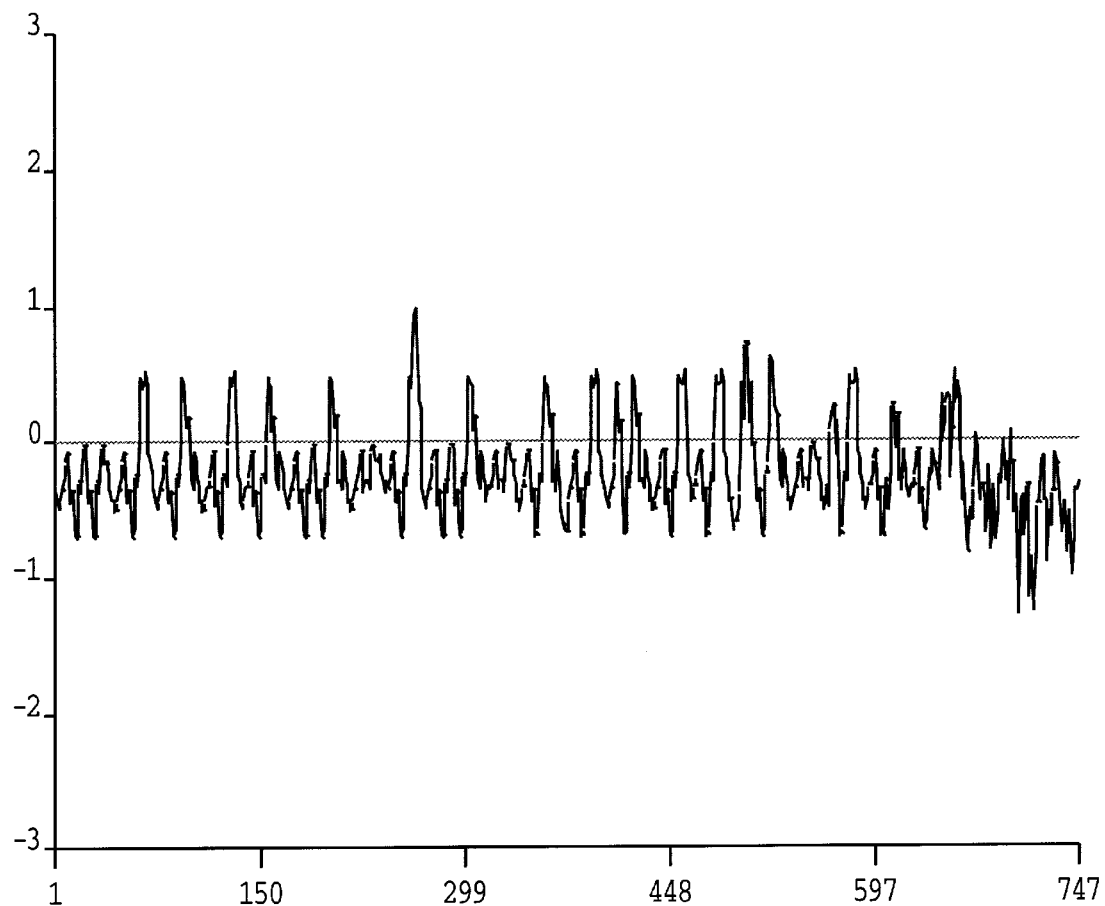

In one embodiment, the invention encompasses a polypeptide comprising the amino acid sequence of SEQ ID NO:1, as shown in FIGS. 1A–1H. FIBR is 582 amino acids in length and has fifteen potential casein kinase II phosphorylation sites at residues T25, S34, T116, S122, S131, S275, S321, S332, S349, T366, S459, S509, T530, S532, and S545; and three potential protein kinase C phosphorylation sites at residues T187, S459, and S519. FIBR has chemical and structural homology with *Nephila clavipes* dragline silk fibroin 1 (GI 1174414; SEQ ID NO:3). In particular, FIBR and *Nephila clavipes* dragline silk fibroin 1 share 12% identity. As illustrated by FIGS. 2A and 2B, FIBR and *Nephila clavipes* dragline silk fibroin 1 have rather similar hydrophobicity plots, with a pattern of alternating hydrophobic and hydrophilic regions. A fragment of SEQ ID NO:2 is from about nucleotide 140 to about nucleotide 157. Northern analysis shows the expression of this sequence in various libraries, at least 52% of which are immortalized or cancerous and at least 43% of which are from inflamed tissues. Of particular note is the expression of FIBR in libraries derived from reproductive (34%), gastrointestinal (18%) and hematopoietic/immune (18%) tissues.

The invention also encompasses FIBR variants. A preferred FIBR variant is one which has at least about 80%, more preferably at least about 90%, and most preferably at least about 95% amino acid sequence identity to the FIBR amino acid sequence, and which contains at least one functional or structural characteristic of FIBR.

The invention also encompasses polynucleotides which encode FIBR. In a particular embodiment, the invention encompasses a polynucleotide sequence comprising the sequence of SEQ ID NO:2, which encodes an FIBR.

The invention also encompasses a variant of a polynucleotide sequence encoding FIBR. In particular, such a variant polynucleotide sequence will have at least about 80%, more preferably at least about 90%, and most preferably at least about 95% polynucleotide sequence identity to the polynucleotide sequence encoding FIBR. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of FIBR.

It will be appreciated by those skilled in the art that as a result of the degeneracy of the genetic code, a multitude of polynucleotide sequences encoding FIBR, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring FIBR, and all such variations are to be considered as being specifically disclosed.

Although nucleotide sequences which encode FIBR and its variants are preferably capable of hybridizing to the nucleotide sequence of the naturally occurring FIBR under appropriately selected conditions of stringency, it may be advantageous to produce nucleotide sequences encoding FIBR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding FIBR and its derivatives without altering the encoded amino acid sequences include the production of RNA transcripts having more desirable properties, such as a greater half-life, than transcripts produced from the naturally occurring sequence.

The invention also encompasses production of DNA sequences which encode FIBR and FIBR derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding FIBR or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (GIBCO/BRL, Gaithersburg, Md.). Preferably, the process is automated with machines such as the Hamilton Micro Lab 2200 (Hamilton, Reno, Nev.), Peltier Thermal Cycler (PTC200: MJ Research, Watertown, Mass.) and the ABI Catalyst and 373 and 377 DNA Sequencers Perkin Elmer).

The nucleic acid sequences encoding FIBR may be extended utilizing a partial nucleotide sequence and employing various methods known ir the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth. Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode FIBR may be used in recombinant DNA molecules to direct expression of FIBR, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express FIBR.

As will be understood by those of skill in the art, it may be advantageous to produce FIBR-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter FIBR-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding FIBR may be ligated to a heterologous sequence to encode a fusion protein. For example, to screen peptide libraries for inhibitors of FIBR activity, it may be useful to encode a chimeric FIBR protein that can be recognized by a commercially available antibody. A fusion protein may also be engineered to contain a cleavage site located between the FIBR encoding sequence and the heterologous protein sequence, so that FIBR may be cleaved and purified away from the heterologous moiety.

In another embodiment, sequences encoding FIBR may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 225–232.) Alternatively, the protein itself may be produced using chemical methods to synthesize the amino acid sequence of FIBR, or a fragment thereof. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of FIBR, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active FIBR, the nucleotide sequences encoding FIBR or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding FIBR and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding FIBR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CAMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding FIBR which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the Bluescript® phagemid (Stratagene, La Jolla, Calif.) or pSport1™ plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding FIBR, vectors based on SV40 or EBV may be used with an appropriate selectable marker.

In bacterial systems, a number of expression vectors may be selected depending upon the use intended for FIBR. For example, when large quantities of FIBR are needed for the induction of antibodies, vectors which direct high level expression of fusion proteins that are readily purified may be used. Such vectors include, but are not limited to, multifunctional *E. coli* cloning and expression vectors such as Bluescript® (Stratagene), in which the sequence encoding FIBR may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Pharmacia Biotech, Uppsala, Sweden) may also be used to express foreign polypeptides as fusion proteins with glutathione S-transferase (GST) In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding FIBR may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express FIBR. For example, in one such system, *Autographa californica* nuclear polyhedrosis virus (AcN?V) is used as a vector to express foreign genes in *Spodoptera frugiperda* cells or in Trichplusia larvae. The sequences encoding FIBR may be cloned into a non-essential region of the virus, such as the polyhedrin gene, and placed under control of the polyhedrin promoter. Successful insertion of sequences encoding FIBR will render the polyhedrin gene inactive and produce recombinant virus lacking coat protein. The recombinant viruses may then be used to infect, for example, *S. frugiperda* cells or Trichoplusia larvae in which FIBR may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding FIBR may be ligated into an adenovirus transcription/translation complex consisting of the late promoter and tripartite leader sequence. Insertion in a non-essential E1 or E3 region of the viral genome may be used to obtain a viable virus which is capable of expressing FIBR in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding FIBR. Such signals include the ATG initiation codon and adjacent sequences. In cases where sequences encoding FIBR and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing FIBR can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk$^-$ or apr$^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, β glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding FIBR is inserted within a marker gene sequence, transformed cells containing sequences encoding FIBR can be identified by the absence of marker gene function. Alternatively, a marker gene can be placed in tandem with a sequence encoding FIBR under the control of a single promoter. Expression of the marker gene in response to induction or selection usually indicates expression of the tandem gene as well.

Alternatively, host cells which contain the nucleic acid sequence encoding FIBR and express FIBR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding FIBR can be detected by DNA-DNA or DNA-RNA hybridization or amplification using probes or fragments or fragments of polynucleotides encoding FIBR. Nucleic acid amplification based assays involve the use of oligonucleotides or oligomers based on the sequences encoding FIBR to detect transformants containing DNA or RNA encoding FIBR.

A variety of protocols for detecting and measuring the expression of FIBR, using either polyclonal or monoclonal antibodies specific for the protein, are known in the art Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on FIBR is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding FIBR include oligolabeling, nick translation, end-labeling, or PCR amplification using a labeled nucleotide. Alternatively, the sequences encoding FIBR, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding FIBR may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode FIBR may be designed to contain signal sequences which direct secretion of FIBR through a prokaryotic or eukaryotic cell membrane. Other constructions may be used to join sequences encoding FIBR to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the FIBR encoding sequence may be used to facilitate purification. One such expression vector provides for expression of a fusion protein containing FIBR and a nucleic acid encoding 6 histidine residues preceding a thioredoxin or an enterokinase cleavage site. The histidine residues facilitate purification on immobilized metal ion affinity chromatography (IMAC). (See, e.g., Porath, J. et al. (1992) Prot. Exp. Purif. 3: 263–281.) The enterokinase cleavage site provides a means for purifying FIBR from the fusion protein. (See, e.g., Kroll, D. J. et al. (1993) DNA Cell Biol. 12:441453.)

Fragments of FIBR may be produced not only by recombinant production, but also by direct peptide synthesis using solid-phase techniques. (See, e.g Creighton, T. E., supra, pp. 55–60.) Protein synthesis may be performed by manual techniques or by automation. Automated synthesis may be achieved, for example, using the Applied Biosystems 431 A Peptide Synthesizer (Perkin Elmer). Various fragments of FIBR may be synthesized separately and then combined to produce the full length molecule.

Therapeutics

Chemical and structural homology exists between FIBR and dragline silk fibroin 1 from *Nephila clavipes* (GI 1174414). In addition, FIBR is expressed in reproductive, cancerous, and inflamed tissues. Therefore, FIBR appears to play a role in connective tissue disorders, reproductive disorders, cancer, and autoimmune/inflammatory disorders.

Therefore, in one embodiment FIBR or a fragment or derivative thereof may be administered to a subject to treat or prevent a connective disorder associated with decreased expression of FIBR. Such connective tissue disorders can include, but are not limited to, osteogenesis imperfecta, Ehlers-Danlos syndrome, chondrodysplasias, Marfan syndrome, Alport syndrome, familial aortic aneurysm, achondroplasia, mucopolysaccharidoses, osteoporosis, osteopetrosis, Paget's disease, rickets, osteomalacia, hyperparathyroidism, renal osteodystrophy, osteonecrosis, osteomyelitis, osteoma, osteoid osteoma, osteoblastoma, osteosarcoma, osteochondroma, chondroma, chondroblastoma, chondromyxoid fibroma, chondrosarcoma, fibrous cortical defect, nonossifying fibroma, fibrous dysplasia, fibrosarcoma, malignant fibrous histiocytoma, Ewing's sarcoma primitive neuroectodermal tumor, giant cell tumor, osteoarthritis, rheumatoid arthritis, ankylosing spondyloarthritis, Reiter's syndrome, psoriatic arthritis, enteropathic arthritis, infectious arthritis, gout, gouty arthritis, calcium pyrophosphate crystal deposition disease, ganglion, synovial cyst, villonodular synovitis, systemic sclerosis, Dupuytren's contracture, hepatic fibrosis, lupus erythematosus, mixed connective tissue disease, epidermolysis bullosa simplex, bullous congenital ichthyosiform erythroderma (epidermolytic hyperkeratosis), nonepidermolytic and epidermolytic palmoplantar keratoderma, ichthyosis bullosa of Siemens, pachyonychia congenita, and white sponge nevus.

In another embodiment, a vector capable of expressing FIBR or a fragment or derivative thereof may be administered to a subject to treat or prevent a connective tissue disorder including, but not limited to, those described above.

In a further embodiment, a pharmaceutical composition comprising a substantially purified FIBR in conjunction with a suitable pharmaceutical carrier may be administered to a subject to treat or prevent a connective tissue disorder including, but not limited to, those provided above.

In still another embodiment, an agonist which modulates the activity of FIBR may be administered to a subject to treat or prevent a connective tissue disorder including, but not limited to, those listed above.

In a further embodiment an antagonist of FIBR may be administered to a subject to treat or prevent a connective tissue disorder associated with increased expression of FIBR. Such a connective tissue disorder may include, but is not limited to, those discussed above. In one aspect, an antibody which specifically binds FIBR may be used directly as an antagonist or indirectly as a targeting or delivery mechanism for bringing a pharmaceutical agent to cells or tissue which express FIBR.

In an additional embodiment, a vector expressing the complement of the polynucleotide encoding FIBR may be administered to a subject to treat or prevent a connective tissue disorder including, but not limited to, those described above.

In a further embodiment, an antagonist of FIBR may be administered to a subject to treat or prevent a reproductive disorder. Such a reproductive disorder may include, but is not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, uterine fibroids, fibrocystic breast disease, galactorrhea; disruptions of spermatogenesis, abnormal sperm physiology, cancer of the testis, cancer of the prostate, benign prostatic hyperplasia, prostatitis, Peyronie's disease, carcinoma of the male breast and gynecomastia. In one aspect, an antibody which specifically binds FIBR may be used directly as an antagonist or indirectly as a targeting or delivery mechanism for bringing a pharmaceutical agent to cells or tissue which express FIBR.

In an additional embodiment, a vector expressing the complement of the polynucleotide encoding FIBR may be administered to a subject to treat or prevent a reproductive disorder including, but not limited to, those described above.

In a further embodiment, an antagonist of FIBR may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle. ovary, pancreas, parathyroid, penis, prostate, salivary glands, skin, spleen, testis, thymus, thyroid, and uterus. In one aspect, an antibody which specifically binds FIBR may be used directly as an antagonist or indirectly as a targeting or delivery mechanism for bringing a pharmaceutical agent to cells or tissue which express FIBR.

In an additional embodiment, a vector expressing the complement of the polynucleotide encoding FIBR may be administered to a subject to treat or prevent a cancer including, but not limited to, those described above.

In a further embodiment, an antagonist of FIBR may be administered to a subject to treat or prevent an autoimmune/inflammatory disorder. Such an autoimmune/inflammatory disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, an antibody which specifically binds FIBR may be used directly as an antagonist or indirectly as a targeting or delivery mechanism for bringing a pharmaceutical agent to cells or tissue which express FIBR.

In an additional embodiment, a vector expressing the complement of the polynucleotide encoding FIBR may be administered to a subject to treat or prevent a an autoimmune/inflammatory disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of FIBR may be produced using methods which are generally known in the art. In particular, purified FIBR may be used to produce antibodies or to screen libraries of pharmaceutical agents to identify those which specifically bind FIBR. Antibodies to FIBR may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with FIBR or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to FIBR have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of FIBR amino acids may be fused with those of another protein, such as KLH, and antibodies to the chimeric molecule may be produced.

Monoclonal antibodies to FIBR may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody gene; to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce FIBR-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for FIBR may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between FIBR and its specific antibody. A two-site. monoclonal-based immunoassay utilizing monoclonal antibodies reactive to two non-interfering FIBR epitopes is preferred, but a competitive binding assay may also be employed. (Maddox, supra.)

In another embodiment of the invention, the polynucleotides encoding FIBR, or any fragment or complement thereof, may be used for therapeutic purposes. In one aspect, the complement of the polynucleotide encoding FIBR may be used in situations in which it would be desirable to block the transcription of the mRNA. In particular, cells may be transformed with sequences complementary to polynucleotides encoding FIBR. Thus, complementary molecules or fragments may be used to modulate FIBR activity, or to achieve regulation of gene function. Such technology is now well known in the art, and sense or antisense oligonucleotides or larger fragments can be designed from various locations along the coding or control regions of sequences encoding FIBR.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding FIBR. (See, e.g., Sambrook, supra; and Ausubel, supra.)

Genes encoding FIBR can be turned off by transforming a cell or tissue with expression vectors which express high levels of a polynucleotide, or fragment thereof, encoding FIBR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding FIBR. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding FIBR.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding FIBR. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polyeationic amino polymers may be achieved using methods which are well known in the art. (See, e.g., Goldman, C. K. et al. (1997) Nature Biotechnology 15:462466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of FIBR, antibodies to FIBR, and mimetics, agonists, antagonists, or inhibitors of FIBR. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of FIBR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal mode Is such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example FIBR or fragments thereof, antibodies of FIBR, and agonists, antagonists or inhibitors of FIBR, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind FIBR may be used for the diagnosis of disorders characterized by expression of FIBR, or in assays to monitor patients being treated with FIBR or agonists, antagonists, or inhibitors )f FIBR. Antibodies useful for diagnostic purposes may be prepared in the same manner as described above for therapeutics. Diagnostic assays for FIBR include methods which utilize the antibody and a label to detect FIBR in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring FIBR, including ELISAs, RIAs, and FACS, are known in the art and provide a basis for diagnosing altered or abnormal levels of FIBR expression. Normal or standard values for FIBR expression are established by combining body fluids or cell extracts taken from normal mammalian subjects, preferably human, with antibody to FIBR under conditions suitable for complex formation. The amount of standard complex formation may be quantitated by various methods, preferably by photometric means. Quantities of FIBR expressed in subject samples, control and disease, from biopsied tissues are compared with the standard values. Deviation between standard and subject values establishes the parameters for diagnosing disease.

In another embodiment of the invention, the polynucleotides encoding FIBR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of FIBR may be correlated with disease. The diagnostic assay may be used to determine absence, presence, and excess expression of FIBR, and to monitor regulation of FIBR levels during therapeutic intervention.

In one aspect, hybridization with PCR probes which are capable of detecting polynucleotide sequences, including genomic sequences, encoding FIBR or closely related molecules may be used to identify nucleic acid sequences which encode FIBR. The specificity of the probe, whether it is made from a highly specific region, e.g., the 5' regulatory region, or from a less specific region, e.g., a conserved motif, and the stringency of the hybridization or amplification (maximal, high, intermediate. or low), will determine whether the probe identifies only naturally occurring sequences encoding FIBR, alleles, or related sequences.

Probes may also be used for the detection of related sequences, and should preferably have at least 50% sequence identity to any of the FIBR encoding sequences. The hybridization probes of the subject invention may be DNA or RNA and may be derived from the sequence of SEQ ID NO:2 or from genomic sequences including promoters, enhancers, and introns of the FIBR gene.

Means for producing specific hybridization probes for DNAs encoding FIBR include the cloning of polynucleotide sequences encoding FIBR or FIBR derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding FIBR may be used for the diagnosis of a disorder associated with expression of FIBR. Examples of such a disorder include, but are not limited to, connective tissue disorders such as osteogenesis imperfecta, Ehlers-Danlos syndrome, chondrodysplasias, Marfan syndrome, Alport syndrome, familial aortic aneurysm, achondroplasia, mucopolysaccharidoses, osteoporosis, osteopetiosis, Paget's disease, rickets, osteomalacia, hyperparathyroidism, renal osteodystrophy, osteonecrosis, osteomyelitis, osteoma, osteoid osteoma, osteoblastoma, osteosarcoma, osteochondroma, chondroma, chondroblastoma, chondromyxoid fibroma, chondrosarcoma, fibrous cortical defect, nonossifying fibroma, fibrous dysplasia, fibrosarcoma, malignant fibrous histiocytoma, Ewing's sarcoma, primitive neuroectodermal tumor, giant cell tumor, osteoarthritis, rheumatoid arthritis, ankylosing spondyloarthritis, Reiter's syndrome, psoriatic arthritis, enteropathic arthritis, infectious arthritis, gout, gouty arthritis, calcium pyrophosphate crystal deposition disease, ganglion, synovial cyst, villonodular synovitis, systemic sclerosis, Dupuytren's contracture, hepatic fibrosis, lupus erythematosus, mixed connective tissue disease, epidermolysis bullosa simplex, bullous congenital ichthyosiform erythroderma (epidermolytic hyperkeratosis), non-epidermolytic and epidermolytic palmoplantar keratoderma, ichthyosis bullosa of Siemens, pachyonychia congenita, and white sponge nevus; reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, uterine fibroids, fibrocystic breast disease, galactorrhea; disruptions of spermatogenesis, abnormal sperm physiology, cancer of the testis, cancer of the prostate, benign prostatic hyperplasia, prostatitis, Peyronie's disease, carcinoma of the male breast and gynecomastia; cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and autoimmune/inflammatory disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding FIBR may be used in Southern or northern analysis, dot blot, or other membrane-based technologies; in PCR technologies; in dipstick, pin, and ELISA assays; and in microarrays utilizing fluids or tissues from patients to detect altered FIBR expression. Such qualitative or quantitative methods are well known in the art.

In a particular aspect, the nucleotide sequences encoding. FIBR may be useful in assays that detect the presence of associated disorders, particularly those mentioned above. The nucleotide sequences encoding FIBR may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding FIBR in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of FIBR, a normal or standard profile for expression is established. This may be accomplished by combining body fluids or cell extracts taken from normal subjects, either animal or human, with a sequence, or a fragment thereof, encoding FIBR, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding FIBR may involve the use of PCR. These oligomers may be chemically synthesized, generated enzymatically, or produced in vitro. Oligomers will preferably contain a fragment of a polynucleotide encoding FIBR, or a fragment of a polynuclectide complementary to the polynucleotide encoding FIBR, and will be employed under optimized conditions for identification of a specific gene or condition. Oligomers may also be employed under less stringent conditions for detection or quantitation of closely related DNA or RNA sequences.

Methods which may also be used to quantitate the expression of FIBR include radiolabeling or biotinylating nucleotides, coamplification of a control nucleic acid, and interpolating results from standard curves. (See, e.g., Melby, P. C. et al. (1993) J. Immunol.

Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding FIBR may be used to generate hybridization probes useful in mapping the naturally occurring genomic sequence. The sequences may be mapped to a particular chromosome, to a specific region of a chromosome, or to artificial chromosome constructions, e.g. human artificial chromosomes (HACs), yeast artificial chromosomes (YACs), bacterial artificial chromosomes (BACs), bacterial P1 constructions, or single chromosome cDNA libraries. (See, e.g., Price, C. M. 1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding FIBR on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, FIBR, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between FIBR and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with FIBR, or fragments thereof, and washed. Bound FIBR is then detected by methods well known in the art. Purified FIBR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding FIBR specifically compete with a test compound for binding FIBR. In this manner, antibodies can be used to detect the presence of any peptide which shares one or more antigenic determinants with FIBR.

In additional embodiments, the nucleotide sequences which encode FIBR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. OVARTUT01 cDNA Library Construction

The OVARTUT01 cDNA library was constructed from tumorous ovarian tissue obtained from a 43-year-old Caucasian female during a bilateral salpingo-oophorectomy. The frozen tissue was homogenized and lysed using a Brinkmann Homogenizer Polytron PT-3000 (Brinkmann Instruments, Westbury, N.Y.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNase-free water, and DNase treated at 37° C. RNA extraction and precipitation were repeated as before. The mRNA was isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Catalog #18248-013, Gibco/BRL). The cDNAs were fractionated on a Sepharose CL4B column (Catalog #275105-01, Pharmacia), and those cDNAs exceeding 400 bp were ligated into pSport I. The plasmid pSport I was subsequently transformed into DH5α™ competent cells (Catalog #18258-012, Gibco/BRL).

II. Isolation and Sequencing of cDNA Clones

Plasmid DNA was released from the cells and purified using the REAL Prep 96 plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokayotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against Gen Bank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al (1997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding FIBR occurs. Abundance and percent abundance are also reported. Abundance directly reflects the number of times a particular transcript is represented in a cDNA library, and percent abundance is abundance divided by the total number of sequences examined in the cDNA library.

V. Extension of FIBR Encoding Polynucleotides

The nucleic acid sequence of Incyte Clone 2257563 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XLPCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2× carbenicillin (2× carb). The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 Jul from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

In another alternative, full-length cDNAs, Expressed Sequence Tags (ESTs), or fragments thereof comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the FIBR-encoding secuences, or any parts thereof, are used to detect, decrease, or inhibit expression of naturally occurring FIBR. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of FIBR. To inhibit transcription, a complementary oligonucleotide is designed from the most unique 5' sequence and used to prevent promoter binding to the coding sequence. To inhibit translation, a complementary oligonucleotide is designed to prevent ribosomal binding to the FIBR-encoding transcript.

IX. Expression of FIBR

Expression of FIBR is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the fill length protein. The signal residues direct the secretion of FIBR into bacterial growth media which can be used directly in the following assay for activity.

X. Demonstration of FIBR Activity

FIBR, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled FIBR, washed, and any wells with labeled FIBR complex are assayed. Data obtained using different concentrations of FIBR are used to calculate values for the number, affinity, and association of FIBR with the candidate molecules.

XI. Production of FIBR Specific Antibodies

FIBR substantially purified using PAGE electrophoresis (see, e.g., Harrington, M. G. (1990) Methods Enzymol. 182:488–495), or other purification techniques, is used to immunize rabbits and to produce antibodies using standard protocols. The FIBR amino acid sequence is analyzed using DNASTAR software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccunimide ester (MBS) to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring FIBR Using Specific Antibodies

Naturally occurring or recombinant FIBR is substantially purified by immunoaffinity chromatography using antibodies specific for FIBR. An immunoaffinity column is constructed by covalently coupling anti-FIBR antibody to an activated chromatographic resin, such as CNBr-activated Sepharose (Pharmacia & Upjohn). After the coupling, the resin is blocked and washed according to the manufacturer's instructions.

Media containing FIBR are passed over the immunoaffinity column, and the column is washed under conditions that allow the preferential absorbance of FIBR (e.g., high ionic strength buffers in the presence of detergent). The column is eluted under conditions that disrupt antibody/FIBR binding (e.g., a buffer of pH 2 to pH 3, or a high concentration of a chaotrope, such as urea or thiocyanate ion), and FIBR is collected.

XIII. Identification of Molecules Which Interact with FIBR

FIBR, or biologically active fragments thereof, are labeled with $^{125}$I Bolton-Hunter reagent. (See, e.g., Bolton et al. (1973) Biochem. J. 133:529 ) Candidate molecules previously arrayed in the wells of a multi-well plate are inculcated with the labeled FIBR, washed, and any wells with labeled FIBR complex are assayed. Data obtained using different concentrations of FIBR are used to calculate values for the number, affinity, and association of FIBR with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEQ ID NO: 1.

2. An isolated and purified polynucleotide variant having at least 90% polynucleotide sequence identity to the polynucleotide of claim 1, as determined using the default parameters of the Clustal algorithm defined by the Megalign program.

3. A composition comprising the polynucleotide of claim 1.

4. An isolated and purified polynucleotide which is completely complementary to the polynucleotide of claim 1.

5. An isolated and purified polynucleotide comprising the polynucleotide sequence of SEQ ID NO:2.

6. An isolated and purified polynucleotide variant having at least 90% polynucleotide sequence identity to the polynucleotide of claim 5, as determined using the default parameters of the Clustal algorithm defined by the Megalign program.

7. An isolated and purified polynucleotide which is completely complementary to the polynucleotide of claim 5.

8. An expression vector containing the polynucleotide of claim 1.

9. A host cell containing the expression vector of claim 8.

10. A method for producing a polypeptide comprising a sequence of SEQ ID NO:1, the method comprising the steps of:

(a) culturing the host cell of claim 9 under conditions suitable for the expression of the polypeptide; and (b) recovering the polypeptide from the host cell culture.

11. A method for detecting a polynucleotide encoding a polypeptide comprising the amino acid sequence of SEQ ID NO:1 in a biological sample containing nucleic acids, the method comprising the steps of:

(a) hybridizing the polynucleotide of claim 7 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample.

12. The method of claim 11 wherein the nucleic acids of the biological sample are amplified by the polymerase chain reaction prior to the hybridizing step.

* * * * *